United States Patent [19]

Greiner et al.

[11] 4,358,684

[45] Nov. 9, 1982

[54] X-RAY DIAGNOSTIC INSTALLATION COMPRISING A TIMING DEVICE

[75] Inventors: Hans-Joachim Greiner, Buckenhof; Werner Saalfrank, Erlangen, both of Fed. Rep. of Germany

[73] Assignee: Siemens Aktiengesellschaft, Berlin & Munich, Fed. Rep. of Germany

[21] Appl. No.: 227,463

[22] Filed: Jan. 22, 1981

[30] Foreign Application Priority Data

Feb. 28, 1980 [DE] Fed. Rep. of Germany ....... 3007621

[51] Int. Cl.$^3$ ......................... A61B 6/00; H05G 1/26; H05G 1/46

[52] U.S. Cl. ...................................... 378/98; 364/414; 378/97

[58] Field of Search .................... 250/416 R, 322, 402; 364/414

[56] References Cited

U.S. PATENT DOCUMENTS 4,047,044 9/1977 Weaver ........................... 250/416 R 4,158,138 6/1979 Hellstrom ........................... 250/402

4,160,906 7/1979 Daniels et al. .................. 250/416 R

OTHER PUBLICATIONS

*OPTIMATIC System for Decentralized Programmed Radiography*, Siemens Aktiengesellschaft, Medical Engineering Group, Erlangen, (1979), pp. 1-26.

*Primary Examiner*—Alfred E. Smith

*Assistant Examiner*—T. N. Grigsby

*Attorney, Agent, or Firm*—Hill, Van Santen, Steadman, Chiara & Simpson

[57] ABSTRACT

In an exemplary embodiment, a timing device sets the fluoroscopy time, and a program setting and display device displays the instantaneous values of the fluoroscopy voltage and current. An arithmetic unit is provided to which signals are supplied which correspond to the fluoroscopy voltage, the fluoroscopy current, and the fluoroscopy time, and which is so designed that it forms the arithmetic mean values of these quantities and brings them to display.

4 Claims, 1 Drawing Figure

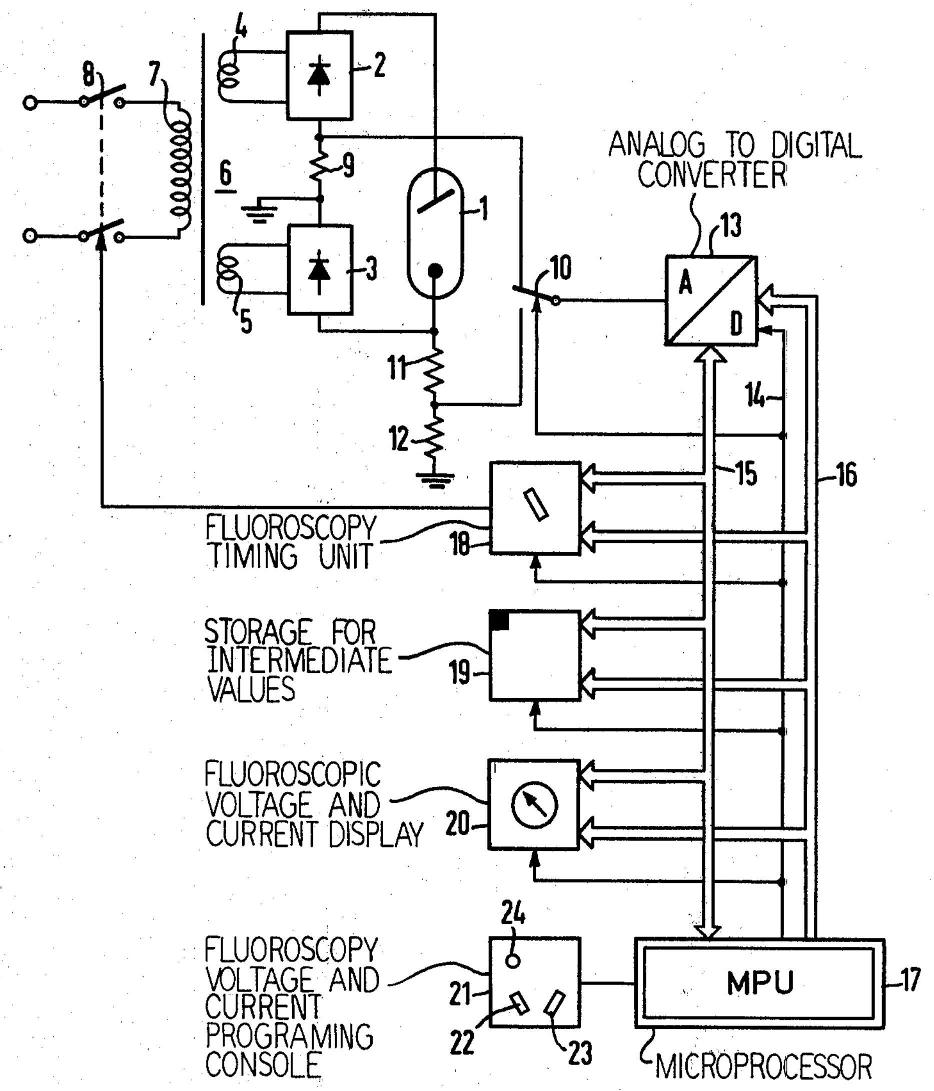
ANALOG TO DIGITAL CONVERTER
A
D
MPU
MICROPROCESSOR
FLUOROSCOPY TIMING UNIT
STORAGE FOR INTERMEDIATE VALUES
FLUOROSCOPIC VOLTAGE AND CURRENT DISPLAY
FLUOROSCOPY VOLTAGE AND CURRENT PROGRAMING CONSOLE
1
2
3
4
5
6
7
8
9
10
11
12
13
14
15
16
17
18
19
20
21
22
23
24

X-RAY DIAGNOSTIC INSTALLATION COMPRISING A TIMING DEVICE

BACKGROUND OF THE INVENTION

The invention relates to an x-ray diagnostic installation comprising a timing device for determining the fluoroscopy time, as well as comprising programming and display means for the preselection and display of selected instantaneous values for a fluoroscopic examination.

A known x-ray diagnostic installation of this type (Siemens brochure: Optimatic System for De-Centralized Programmed Radiography, pages 16 and 17, order No. MR 65/1207) is equipped with rotary type switches for preselection of the tube voltage and of the tube current. Their instantaneous values are brought to display during fluoroscopy via dial (or scale-and-pointer) instruments, so that it is possible to read off the instantaneous radiation exposure of the patient. A mechanical short-term timer serves the purpose of determining the fluoroscopy time. It indicates the residual time still remaining, respectively, and interrupts the x-ray tube current circuit upon expiration of the fixed fluoroscopy time for the purpose of terminating the fluoroscopy operation. If the voltage and current values remain constant, then it is possible to directly read them off as mean (or average) values during the fluoroscopy.

In the case of an x-ray diagnostic installation comprising an automatic dose regulation, in which the parameters of the x-ray tube are constantly varied, in the known x-ray diagnostic installation, a determination of the mean value and thus an ascertainment of the x-ray dose to which the patient is exposed is very difficult.

SUMMARY OF THE INVENTION

The invention proceeds from the object of creating an x-ray diagnostic installation of the type initially cited which renders possible a simple determination of the mean values of the fluoroscopy data for the purpose of determining the radiation exposure.

This object is solved in accordance with the invention in that an arithmetic unit is provided to which are supplied signals corresponding to the fluoroscopy tube voltage, the fluoroscopy current, and the fluoroscopy time, and which arithmetic unit is so designed that it forms the arithmetic mean values of the quantities and displays them. Through this arrangement it is possible to determine in a simple fashion the radiation dose which has acted upon the patient.

It has proven expedient that the arithmetic unit is so designed that during fluoroscopy the instantaneous values are displayed and, subsequent to termination of the fluoroscopy, the mean values are formed and brought to display. A simple and expedient construction as well as good read-off properties can be obtained if an analog-to-digital converter digitalizes the tube voltage values and tube current values, if the timing installation contains a digital clock, and if the arithmetic unit is designed as a microprocessor which processes the digital values of the analog to digital converter and of the time unit. In addition, it is expedient if storage means for intermediate storage of the values calculated during the fluoroscopy are connected with the arithmetic unit. A larger comprehensive view of the fluoroscopy data is obtained if the display device exhibits means for the simultaneous display of the values for tube voltage and tube current as well as the fluoroscopy time determined by the time installation.

The invention shall be explained in greater detail in the following on the basis of an exemplary embodiment illustrated on the accompanying drawing sheet; and other objects, features and advantages will be apparent from this detailed disclosure and from the appended claims.

BRIEF DESCRIPTION OF THE DRAWING

The single FIGURE is a diagrammatic view showing an x-ray diagnostic installation in accordance with the present invention.

DETAILED DESCRIPTION

In the drawing an x-ray tube 1 is illustrated whose anode is connected with the positive pole of a rectifier 2 and whose cathode is connected with a negative pole of a rectifier 3. The a.c. inputs of the rectifiers 2 and 3 are connected to the secondary windings 4 and 5 of a transformer 6 whose primary winding 7 is capable of being connected to an a.c. mains via a two pole switch 8.

The d.c. voltage poles of the rectifiers 2 and 3 are connected via a low-ohmic resistance 9 which has one terminal connected to ground. The voltage resulting at the other terminal of the resistance 9 corresponds to the current of the x-ray tube 1. This voltage is tapped and supplied to one terminal of a switch 10. The cathode of the x-ray tube is connected to ground via a voltage divider consisting of resistances 11 and 12. The output of the voltage divider 11, 12 is connected with an additional terminal of the switch 10.

The third terminal of the switch 10 is connected to an A/D converter 13 (analog-to-digital converter) which digitalizes the received analog voltage values. The A/D converter 13 is connected via a control 14, a data line 15, and an address line 16, with a microprocessor 17. There are furthermore connected to the lines 14, 15, and 16, a timer installation 18 with a digital clock storage means 19 and a display device 20.

A switching or console unit 21 is connected with the microprocessor 17 which switching unit exhibits programming means for adjustment of the fluoroscopy values. With rotary type switches 22 and 23 the tube voltage and the tube current can be adjusted.

The method of operation of the circuit is described in the following.

A switch 24 starts the fluoroscopy operation. The microprocessor 17 sets the storage means 19 and the timing device 18 to zero and starts the timing device 18 which closes contacts 8 to apply mains voltage. Controlled by the microprocessor 17, the measured current values and voltage values are sequentially connected via switch 10 to the input of the A/D converter 13, and are read via data line 15 into the microprocessor 17. The microprocessor 17 then effects display of the just received (essentially instantaneous) current and voltage values on the display device 20 and storage in the storage means 19.

If the adjusted current values and voltage values as read by the microprocessor 17 (via switch 10 and converter 13) are found to vary, the accumulated (elapsed) time value is read out of the timing device 18 and stored in the storage means 19, along with the products obtained by multiplying the current and voltage values each by a time duration value. At the time that the results of such multiplication operations are stored in storage means 19, namely the current-time product and the voltage-time product, respectively, the new actual current and voltage values are also stored in storage means 19. If a deviation from the stored new actual values is found, this operation is repeated, and the new elapsed time value is read out from the timing device 18, subtracted from the preceding time value previously stored in the memory installation 19 and the time duration value so obtained is multiplied with the previously stored actual current and voltage values and each product so obtained is added to the corresponding previously stored product (so as to maintain an accumulated total).

When the fluoroscopy is terminated, that is when the fluoroscopy time selected at the timing device 18 at commencement of the fluoroscopy is attained, the mains voltage is switched off. In the microprocessor 17 the values stored in the storage means 19 are read out. The accumulated sum of the voltage-time products and the accumulated sum of the current-time products are each divided by the overall (or total elapsed) time in the time memory. The obtained mean values are brought to display at display 20 (e.g. in place of the last instantaneous values). Also the overall (or total) time can appear on the display device 20.

The mean value computation is also possible in a different fashion. Thus, for example, the voltage and current measured values read via components 10, 13 and 17 can be added, in a fixed timing (or clock) pulse, to the values stored in the storage means 19. Subsequent to termination of fluoroscopy these added-up values are divided by the number of timing (or clock) pulse intervals present in the storage means 19. During the fluoroscopy time, in addition to the actual values of the tube voltage and of the tube current, also the fluoroscopy time of the timing device 18 can be displayed.

Through the inventive embodiment of an x-ray diagnostic installation it is made possible to display the instantaneous values of the tube voltage and of the tube current during fluoroscopy and, after switching-off of the fluoroscopy, to form the time-weighted mean values and display the results.

It will be apparent that many modifications and variations may be effected without departing from the scope of the novel concepts and teachings of the present invention.

Supplementary Discussion

For the case where microprocessor 17 is to form the mean values of fluoroscopy voltage and current by monitoring for departures from setpoint values, the setpoint values are introduced by selector switches 22 and 23 and may be placed in registers directly accessible to microprocessor 17. Then during fluoroscopy, the microprocessor 17 compares each instantaneous value of voltage and current from converter 13. So long as the "instantaneous" values equal the setpoint values, the microprocessor merely effects the display of the successive instantaneous values. The sampling action of converter 13 is controlled via selector line 16 and may take place sufficiently frequently so that no significant variations in voltage or current will be missed, and so that the values displayed will essentially represent instantaneous values.

If a sampled value from converter 13 is found to deviate from the corresponding setpoint value, microprocessor effectively may calculate the product obtained by multiplying the setpoint value by the elapsed time at such sampling instant. This product is stored as an intermediate accumulated value in storage 19. At the same time the first deviating sample value and its associated first elapsed time are also stored. Then with the next sampling of the same parameter, the parameter value may be compared with the first deviating sample value. As soon as a further (second) deviation is found, the second deviating sample value and the associated second elapsed time are stored in storage 19, and the product of the first deviating sample value with the difference between the second elapsed time value for such value and the first elapsed time value is calculated and added to the intermediate accumulated value in storage 19. By following this procedure, the final accumulating value divided by the final elapsed time will give the mean value for the parameter. As a simple example, if the setpoint value of voltage is 100 kilovolts and a deviation to 101 kilovolts occurs at an elapsed time of two seconds, then an intermediate accumulated value of 200 kilovolt seconds will be recorded. If no further deviation occurs and fluoroscopy terminates at an elapsed time of three seconds, then a time value of three minus two seconds is multiplied by 101 kilovolts and the product (101 kilovolt seconds) added to form a final accumulated value of 301 kilovolt seconds. Dividing by the total elapsed time of three seconds, a mean value of 100.3 kilovolts is obtained and displayed promptly at the end of fluoroscopy.

We claim as our invention:

1. In an x-ray diagnostic installation comprising a timing device (18) for determining the fluoroscopy time, and programming and display means (21) for preselection of desired fluoroscopic parameters and display of instantaneous values of such fluoroscopic parameters, the improvement comprising an arithmetic unit (17) having means (15) for supplying thereto signals corresponding to the fluoroscopy tube voltage, the fluoroscopy tube current, and a measure of the fluoroscopy time, and being operable to form the arithmetic mean values of tube voltage and current and to effect the display of such mean values.

2. An x-ray diagnostic installation according to claim 1, with means comprising said arithmetic unit (17) operable during fluoroscopy to effect display of instantaneous values of tube voltage and current, while following termination of the fluoroscopy, the mean values are formed and brought to display.

3. An x-ray diagnostic installation according to claim 1, with analog-to-digital converter means (13) for digitalizing the tube voltage values and the tube current values for supply to the arithmetic unit (17), said timing device (18) having a digital time unit for supplying a measure of fluoroscopy time to the arithmetic unit, a microprocessor (17) forming said arithmetic unit and being operable to process the digital values from the analog-to-digital-converter (13) and from the timing device (18) to form said means values of the tube voltage and current.

4. An x-ray diagnostic installation according to claim 1, with the arithmetic unit (17) having storage means (19) operable for intermediate storage of values calculated during fluoroscopy.

* * * * *